ative Patent [19] [11] 4,345,934
Fujimoto [45] Aug. 24, 1982

[54] METHOD OF PRODUCING HYBRID CEREAL GRAIN SEEDS BY APPLICATION OF 1-ARYL-1,4-DIHYDRO-4-OXO(THIO)-PYRIDAZINES

[75] Inventor: Ted T. Fujimoto, Warminster, Pa.

[73] Assignee: Rohm and Haas Company, Philadelphia, Pa.

[21] Appl. No.: 15,029

[22] Filed: Feb. 26, 1979

Related U.S. Application Data

[63] Continuation-in-part of Ser. No. 776,394, Mar. 10, 1977, abandoned.

[51] Int. Cl.³ ............................................. A01N 43/58
[52] U.S. Cl. ....................................................... 71/92
[58] Field of Search ............................................ 71/92

[56] References Cited

U.S. PATENT DOCUMENTS 2,454,742 11/1948 Morgan ............................... 260/250
2,835,671 5/1958 Staehelin ............................ 260/250

FOREIGN PATENT DOCUMENTS 762141 11/1956 United Kingdom .

OTHER PUBLICATIONS

Wiley et al., J. Am. Chem. Soc., vol. 78, (1955), p. 624.
Morgan, J. Am. Chem. Soc., vol. 70, (1948), p. 2253.

*Primary Examiner*—Catherine L. Mills

*Attorney, Agent, or Firm*—Lester E. Johnson

[57] ABSTRACT

Compounds of the formula

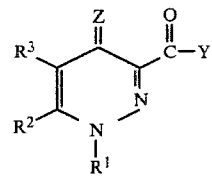

wherein
$R^1$ is aryl or substituted aryl,
$R^2$ is alkyl, or aryl,
$R^3$ is hydrogen, alkyl, aralkyl, or halogen, or
$R^2$ and $R^3$ taken together are $-(CH_2)_n-$ where n is 3 to 8
Z is oxygen or sulfur, and
Y is the group $Z'R^4$ or $NR^5R^6$ wherein $Z'$ is oxygen or sulfur,
$R^4$ is hydrogen, alkoxyalkyl, alkyl, cycloalkyl, cycloalkylalkyl, haloalkyl, phenyl or benzyl or a cation $R^5$ and $R^6$ are independently hydrogen or alkyl or when $R^5$ is hydrogen, $R^6$ is hydroxy or an alkyl metal salt thereof. These compounds are active as plant growth regulators, and particularly as chemical hybridization agents.

23 Claims, No Drawings

METHOD OF PRODUCING HYBRID CEREAL GRAIN SEEDS BY APPLICATION OF 1-ARYL-1,4-DIHYDRO-4-OXO(THIO)-PYRIDAZINES

CROSS-REFERENCE TO RELATED APPLICATION

This application is a continuation-in-part application of U.S. application Ser. No. 776,394 filed Mar. 10, 1977, now abandoned.

This invention relates to novel compounds which show activity as plant growth regulators, particularly as chemical hybridization agents, to growth regulant compositions which comprise these compounds, and to methods of regulating the growth of plants, particularly by inducing selective male sterility, with these compounds and compositions.

The cereal grains, such as corn, wheat, rice, rye, barley, oats, millets, sorghum, triticale, and teff and forage crops such as those disclosed in Scientific American Vol. 234, pg. 61-69, February, 1976 by Harlow J. Hodgson are among the major potential food crops throughout the world. This importance has led to extensive research to improve both the productivity and food value of these crops. One of the most important approaches taken to improve the quality and yield of the cereal grains has been hybridization. While hybridization has been an effective technique for some crops, most notably corn, there have been a number of problems with present techniques. For example, corn hybridization requires time-consuming hand detasseling or inefficient mechanical detasseling, possibly injuring the corn plant. Corn, and wheat hybridization by means of cytoplasmic male sterile varieties can only be done with a limited genetic base, requiring a maintainer line and a restorer line. Furthermore, cytoplasmic male sterile techniques with wheat necessitate a highly sophisticated approach to deal with the genetic complexities of this crop, and great success has not yet been achieved in developing a suitable approach. Since the induction of selective male sterility by chemical means would obviate many of the problems confronting the present hybridization techniques, new compounds which selectively produce the desired sterility would be extremely desirable in dependably and economically supplying the male sterile plants needed for hybridization.

A new class of compounds has now been found which can be used to induce selective male sterility in cereal grains. The compounds of the invention are 1,4-dihydro-4-oxo(thio)-pyridazines having the formula

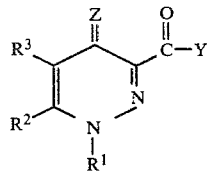

wherein $R^1$ is a phenyl or naphthyl group or a substituted phenyl or naphthyl group, preferably having up to three substituents having a total of up to 6 carbon atoms, $R^2$ is an alkyl group, preferably having up to 4 carbon atoms, or phenyl, and $R^3$ is a hydrogen atom, an alkyl group, preferably having up to 4 carbon atoms, or a halogen atom, preferably a bromine or a chlorine atom, benzyl or phenethyl, or $R^2$ and $R^3$ taken together are $-(CH_2)_n-$ where n is an integer from 3 to 8 preferably from 3 to 5, Z is oxygen or sulfur, and Y is the group $Z'R^4$ or $NR^5R^6$ wherein $Z'$ is oxygen or sulfur, $R^4$ is a hydrogen atom or an agronomically acceptable salt thereof; an alkyl group preferably having up to 12 carbon atoms most preferably up to 4 carbon atoms; an alkoxyalkyl group preferably having up to 12 carbon atoms most preferably up to 4 carbon atoms; a cycloalkyl group having a carbon atom ring of from 3 to 8 carbon atoms, preferably 6 carbon atoms; a cycloalkylalkyl group having a carbon atom ring of from 3 to 8 carbon atoms preferably 6 carbon atoms and an alkyl chain of up to 4 carbon atoms preferably a methylene group; a haloalkyl group having up to 12 carbon atoms preferably chloro, bromo or iodoalkyl of up to 5 carbon atoms, more preferably bromopropyl, chlorobutyl or iodopentyl; a phenyl, naphthyl or benzyl group or a phenyl, naphthyl or benzyl group substituted with up to three substituents having a total of up to 6 carbon atoms; or a cation, $R^5$ and $R^6$ are independently selected from the group consisting of hydrogen or alkyl of up to 4 carbon atoms or alkyl of up to 4 carbon atoms substituted with carboxy or $(C_1-C_4)$alkoxycarbonyl or the agronomically acceptable salt thereof or when $R^5$ is hydrogen $R^6$ is hydroxyl or an alkali metal salt thereof.

In a preferred embodiment of the invention,

is a carboxy group or a salt thereof, $R^2$ is a methyl group, $R^3$ is a hydrogen atom or a halogen atom, and $R^1$ is a substituted phenyl group.

When the group Y is a salt of a carboxy group, an alkali metal, alkaline earth metal, or transition metal can provide the cation. The cation can also be an ammonium or substituted ammonium group. Representative metal salt cations include alkali metal cations, which are preferred, such as sodium, potassium, lithium, or the like, alkaline earth metal cations, such as calcium, magnesium, barium, strontium, or the like, or heavy metal cations, such as zinc, manganese, cupric, cuprous, ferric, ferrous, titanium, aluminum, or the like.

Among the ammonium salts are those of the formula

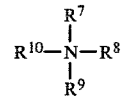

in which $R^7$, $R^8$, $R^9$ and $R^{10}$ are individually a hydrogen atom, a hydroxy group, a $(C_1-C_4)$alkoxy group, a $(C_1-C_{20})$alkyl group, a $(C_3-C_8)$alkenyl group, a $(C_3-C_8)$alkynyl group, a $(C_2-C_8)$hydroxy alkyl group, a $(C_2-C_8)$alkoxyalkyl group, a $(C_2-C_6)$aminoalkyl group, a $(C_2-C_6)$haloalkyl group, a substituted or unsubstituted phenyl group, a substituted or unsubstituted phenylalkyl group, having up to 4 carbon atoms in the alkyl moiety, an amino or alkyl-substituted amino group, or any two of $R^7$, $R^8$, $R^9$ or $R^{10}$ can be taken together to form with the nitrogen atom a 5- or 6-member heterocyclic ring, optionally having up to one additional hetero oxygen, nitrogen, or sulfur atom in the ring, and preferably saturated, such as a piperidine, morpholine, pyrrolidine or piperazine ring, or the like, or any three of $R^7$, $R^8$, $R^9$ or $R^{10}$ can be taken together to form with the nitrogen atom a 5- or 6-member optionally substituted aromatic heterocyclic ring, such as pyrrole, pyridine, nicotine or histamine. When the ammonium group contains a substituted alkyl, substituted phenyl, or substituted phenylalkyl group, the substituents will generally be selected from halogen atoms, $(C_1-C_8)$alkyl groups, $(C_1-C_4)$alkoxy groups, hydroxy groups, nitro groups, trifluoromethyl groups, cyano groups, amino groups, $(C_1-C_4)$alkylthio groups, and the like. Such substituted phenyl groups preferably have up to two such substituents. Representative ammonium cations include ammonium, dimethylammonium 2-ethylhexylammonium, bis(2-hydroxyethyl)ammonium, t-octylammonium, 2-hydroxyethylammonium, morpholinium, piperidinium, 2-phenethylammonium, 2-methylbenzyl-ammonium, n-hexylammonium, triethylammonium, trimethylammonium, tri(n-butyl)ammonium, methoxy-ethylammonium, diisopropylammonium, pyridinium, diallylammonium, pyrazolium, propargylammonium, dimethylhydrazinium, hydroxyammonium, methoxyammonium, dodecylammonium, octadecylammonium, 4-dichlorophenyl-ammonium, 4-nitrobenzylammonium, benzyltrimethyl-ammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like.

Representative embodiments of $R^1$ include phenyl groups substituted with alkyl groups, preferably having up to 4 carbon atoms, aryl groups, preferably phenyl or substituted phenyl groups, alkoxy groups, preferably having up to 4 carbon atoms, phenoxy or substituted phenoxy groups, halogen atoms, such as fluorine, chlorine, bromine, and iodine atoms, nitro groups, perhaloalkyl groups, such as trifluoromethyl groups, alkoxyalkyl groups, preferably having up to 6 carbon atoms, alkoxyalkoxy groups, preferably having up to 6 carbon atoms, amino groups, alkyl or dialkyl amino groups, preferably having up to 4 carbon atoms in each alkyl substituent, cyano groups, carbalkoxy groups, preferably having up to 4 carbon atoms in the alkoxy moiety, carboxy groups, carbamoyl groups, alkyl or dialkyl carbamoyl groups, preferably having up to 4 carbon atoms in each alkyl substituent, sulfo groups, sulfonamide groups, alkylcarbonyl or carboxyalkyl groups, preferably having up to 4 carbon atoms in the alkyl moiety, alkanoyloxy groups, preferably having up to 4 carbon atoms, haloalkyl groups, alkanoylamido groups, preferably having up to 4 carbon atoms, alkylthio groups, preferably having up to 4 carbon atoms, alkylsulfinyl groups, preferably having up to 4 carbon atoms, alkylsulfonyl groups, preferably having up to 4 carbon atoms, and the like. Preferably, the substituted phenyl group will have up to three of the above substituents and the substituents will have a total of up to six carbon atoms. The most preferred substituents on the phenyl group are 1 or 2 halogen atoms, a $(C_1-C_4)$alkyl, preferably methyl, group, a $(C_1-C_4)$alkoxy, preferably methoxy group, $(C_1-C_4)$ alkylthio, $(C_1-C_4)$ alkylsulfinyl, $(C_1-C_4)$ alkyl sulfonyl or a trifluoromethyl group.

Typical compounds within the scope of this invention include:

1-phenyl-1,4-dihydro-4-oxo-6-methylpyridazine-3-carboxylic acid
1-(4-chlorophenyl)-1,4-dihydro-4-oxo-6-methylpyridazine-3-carboxylic acid
1-(4-bromophenyl)-1,4-dihydro-4-oxo-6-methylpyridazine-3-carboxylic acid
1-(4-iodophenyl)-1,4-dihydro-4-oxo-6-methylpyridazine-3-carboxylic acid
1-(3-fluorophenyl)-1,4-dihydro-4-oxo-6-methylpyridazine-3-carboxylic acid
1-(3-chlorophenyl)-1,4-dihydro-4-oxo-6-methylpyridazine-3-carboxylic acid
1-(3-bromophenyl)-1,4-dihydro-4-oxo-6-methylpyridazine-3-carboxylic acid
1-(3,4-dichlorophenyl)-1,4-dihydro-4-oxo-6-methylpyridazine-3-carboxylic acid
1-(2-fluorophenyl)-1,4-dihydro-4-oxo-6-methylpyridazine-3-carboxylic acid
1-(2-chlorophenyl)-1,4-dihydro-4-oxo-6-methylpyridazine-3-carboxylic acid
1-(4-trifluoromethylphenyl)-1,4-dihydro-4-oxo-6-methylpyridazine-3-carboxylic acid
1-(3-trifluoromethylphenyl)-1,4-dihydro-4-oxo-6-methylpyridazine-3-carboxylic acid
1-phenyl-1,4-dihydro-4-oxo-6-ethylpyridazine-3-carboxylic acid
1-(4-chlorophenyl)-1,4-dihydro-4-oxo-6-ethylpyridazine-3-carboxylic acid
1-(4-fluorophenyl)-1,4-dihydro-4-oxo-6-ethylpyridazine-3-carboxylic acid
1-(3,4-dichlorophenyl)-1,4-dihydro-4-oxo-6-ethylpyridazine-3-carboxylic acid
1-phenyl-1,4-dihydro-4-oxo-6-propylpyridazine-3-carboxylic acid
1-phenyl-1,4-dihydro-4-oxo-5,6-dimethylpyridazine-3-carboxylic acid
1-(4-chlorophenyl)-1,4-dihydro-4-oxo-5,6-dimethylpyridazine-3-carboxylic acid
1-phenyl-1,4-dihydro-4-oxo-5-ethyl-6-methylpyridazine-3-carboxylic acid
1-phenyl-1,4-dihydro-4-oxo-5,6-diethylpyridazine-3-carboxylic acid
1-(4-methylphenyl)-1,4-dihydro-4-oxo-6-methylpyridazine-3-carboxylic acid
1-(2,4,6-trichlorophenyl)-1,4-dihydro-4-oxo-6-methylpyridazine-3-carboxylic acid
1-(3-ethoxyphenyl)-1,4-dihydro-4-oxo-6-ethylpyridazine-3-carboxylic acid
1-(4-methylthiophenyl)-1,4-dihydro-4-oxo-6-methylpyridazine-3-carboxylic acid
1-(3-cyanophenyl)-5-bromo-1,4-dihydro-4-oxo-6-ethylpyridazine-3-carboxylic acid
1-phenyl-5-bromo-1,4-dihydro-4-oxo-6-methylpyridazine-3-carboxylic acid
1-(3-chlorophenyl)-5-chloro-1,4-dihydro-4-oxo-6-methylpyridazine-3-carboxylic acid
1-(4-chlorophenyl)-5-bromo-1,4-dihydro-4-oxo-6-ethylpyridazine-3-carboxylic acid,
1-(2-chloro-4-methyl)-1,4-dihydro-4-oxo-6-methylpyridazine-3-carboxylic acid
1-(4-chlorophenyl)-1,4-dihydro-4-oxo-6-phenylpyridazine-3-carboxylic acid
1-(4-trifluoromethylphenyl)-1,4-dihydro-4-oxo-5-phenethyl-6-methylpyridazine-3-carboxylic acid 1-(3,4-dichlorophenyl)-1,4-dihydro-4-oxo-6-butyl-pyridazine-3-carboxylic acid 1-(4-chlorophenyl)-1,4-dihydro-4-oxo-5,6-cyclohexa[b]-pyridazine-3-carboxylic acid 1-(4-chlorophenyl)-1,4-dihydro-4-oxo-5-propyl-6-methylpyridazine-3-carboxylic acid 1-phenyl-1,4-dihydro-4-thio-6-methylpyridazine-3-carboxylic acid 1-(3-chlorophenyl)-1,4-dihydro-4-thio-6-ethylpyridazine-3-carboxylic acid and the like, and the salts, esters and amides of the above acids.

The compounds of the invention can be prepared by several convenient preparative routes. In the first method, a 4-hydroxy-2-pyrone of the formula

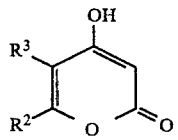

wherein $R^3$ is a hydrogen atom, an aralkyl group or an alkyl group and $R^2$ is defined above, or a salt of a pyrone of Formula II, prepared by treating the pyrone with an equivalent of a suitable aqueous base such as potassium or sodium hydroxide, acetate, or carbonate, is reacted at about $-10°$ to about 50° C. in a polar solvent, such as water, methanol, ethanol, glyme, dimethylformamide, or the like, with a diazonium salt, such as diazonium chloride, prepared by conventional diazotization technique from an amine of the formula

wherein $R^1$ is as defined above. The product hydrazone, which has the formula

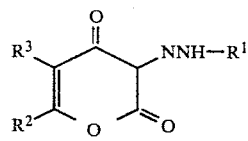

wherein $R^1$, $R^2$, and $R^3$ are as defined above, is then treated with either an aqueous acid, such as hydrochloric acid, trifluoroacetic acid, sulfuric acid, methanesulfonic acid, nitric acid, or the like, or an aqueous base, such as sodium carbonate, sodium hydroxide, or an alcoholic secondary amine such as morpholine, piperidine, dialkyl amine and the like, at a temperature of about 0° to about 150° C., preferably about 40° to about 100° C., to yield, by a rearrangement, a pyridazinone of the formula

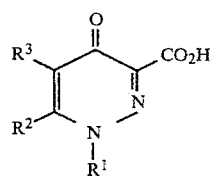

or salt thereof wherein $R^1$, $R^2$, and $R^3$ are as defined above.

The pyridazinones of the invention in which $R^3$ is a halogen atom can be prepared by reacting the corresponding pyridazinones in which $R^3$ is a hydrogen atom with one equivalent of a halogenating agent such as bromine, chlorine, sulfuryl bromide, sulfuryl chloride, or the like in a suitable inert solvent such as hexane, benzene, ethylene dichloride, methanol, or the like, at a temperature of about 0° to 50° C., preferably at room temperature.

Salts of the pyridazinones of Formula V and their 5-halo analogues can be prepared by conventional techniques, such as by neutralization with an appropriate inorganic or organic base, in a solvent such as water or methanol.

Esters of the pyridazinone of Formula V are prepared by esterification with a suitable alcohol, preferably a $(C_1-C_{12})$alkanol. One convenient technique is a Fischer esterification, using anhydrous hydrochloric acid or sulfuric acid as a catalyst and the alcohol as the solvent. This esterfication is generally carried out at about 35° to about 150° C., optionally using an inert cosolvent such as methylene chloride, ethylene chloride, diethyl ether, toluene, xylene, or the like.

Another convenient esterification technique is the reaction of the pyridazinone acylhalide formed as above with an appropriate alcohol utilizing the alcohol or any inert cosolvent for the reaction media. Alternatively a thionyl halide can be utilized to first form a halosulfinite with the appropriate alcohol and this halosulfinite can then be reacted with the pyridazinone carboxylic acid to form the appropriate ester. These esterification procedures can be carried out at about 0° to about 80° C. The alcohol of the ester can also be used as the solvent in this Reaction.

Yet another esterification technique involves the use of a halo carboxylate to form a pyridazinone acylanhydride followed by either thermal decomposition to eliminate carbon dioxide and form the desired ester or addition of an equimolar (or excess) amount of the alcohol of the ester, to form the desired ester. This reaction can initially be run at about 0° C. and the temperature increased until the evolution of carbon dioxide has ceased. This reaction is carried out in the presence of an acid scavenger in an inert solvent. The thioesters of the invention can be prepared as above by the replacement of a thioalcohol.

The pyridazinone carbamides of the invention can be prepared by standard synthetic routes such as the reaction of the acylhalide discussed above with an appropriate amine in an inert solvent at about 0° to about 150° C. Another convenient amination route utilizes the reaction of the pyridazinone carboxylic acid with an appropriate halocarboxylate to first form an acylanhydride which in turn is reacted with an appropriate amine at temperatures at about 25° to about 110° C. in an inert solvent again with the evolution of carbon dioxide to form the appropriate carbamide.

The following examples will further illustrate the compounds of the invention and their preparation, but are not intended to limit the invention in any way. All temperatures are in degrees Celsius and parts and percentages are by weight, unless otherwise indicated.

EXAMPLE 3

Preparation of 1-(4-iodophenyl)-1,4-dihydro 4-oxo-6-methylpyridazine-3-carboxylic acid 4-hydroxy-6-methyl-2-pyrone (11.82 g) is suspended in 375 mls water. 9.95 g of anhydrous sodium carbonate is added to effect solution of the pyrone.

In a separate flask, 21.35 g of 4-iodoaniline is mixed with 37.5 mls concentrated hydrochloric acid and 46.5 mls water. A solution of 7.13 g sodium nitrite in 24 ml water is then added slowly, maintaining a reaction temperature below 10° C.

The cold diazonium ion solution is added rapidly to the previously prepared 4-hydroxy-6-methyl-2-pyrone solution. A yellowish-orange precipitate forms. This is collected by filtration and then suspended in 500 ml concentrated hydrochloric acid. The resulting suspension is refluxed for two hours. It is then cooled and diluted with water to give a precipitate of 1-(4-iodophenyl)-1,4-dihydro-4-oxo-6-methylpyridazine-3-carboxylic acid. This material can be recrystallized from acetone to yield 11.2 gms of pure product (mp 241°-2°, decomposition).

EXAMPLE 4

Preparation of 1-(4-bromophenyl)-1,4-dihydro-4-oxo-6-methylpyridazine-3-carboxylic acid 4-hydroxy-6-methyl-2-pyrone (14.18 g) is suspended in 450 mls of water. 11.94 gms anhydrous sodium carbonate is added to effect solution.

In a separate flask, 20.12 gms of 4-bromoaniline is dissolved in 45 gms of concentrated hydrochloric acid and 56 mls water. A solution of 8.56 gms sodium nitrite in 29 mls water is then slowly added, maintaining a reaction temperature below 10° C.

The cold diazonium ion solution is added rapidly (with stirring) to the previously prepared 4-hydroxy-6-methyl-2-pyrone solution. A thick slurry of the resulting diazonium ion-pyrone coupling product is formed. This is filtered and washed several times with water. The resulting filter cake is transferred to a flask containing 500 mls of concentrated hydrochloric acid. The mixture is brought to reflux. After 90 minutes the reaction mixture is cooled and diluted with water. A precipitate of 1-(4-bromophenyl)-1,4-dihydro-4-oxo-6-methylpyridazine-3-carboxylic acid is formed. This material can be recrystallized from acetone to yield 20.5 gms of pure product. (mp=243°, decomposition).

EXAMPLE 10

Preparation of 1-(4-fluorophenyl)-1,4-dihydro-4-oxo-6-methylpyridazine-3-carboxylic acid 4-Hydroxy-6-methyl-2-pyrone (7.88 g) is suspended in 250 ml water, and 6.63 g of anhydrous sodium carbonate is added to the suspension to effect solution of the pyrone.

In a separation flask, 7.22 g of 4-fluoroaniline is mixed with 25 ml concentrated hydrochloric acid and 31 ml water. The resulting solution is maintained at about 5° to 10° and a solution of 4.75 g of sodium nitrite in 16 ml of water is added. The resulting solution of 4-fluorophenyldiazonium chloride is added dropwise to the stirred pyrone solution, while maintaining the temperature at about 5° to 10°, and the pH at about 8 to 9 by adding small amounts of aqueous sodium hydroxide.

The resulting hydrazone is refluxed for about 2 hours with 500 ml of concentrated hydrochloric acid. Cooling and filtration yields 10.2 g of 1-(4-fluorophenyl)-1,4-dihydro-4-oxo-6-methylpyridazine-3-carboxylic acid which is recrystallized from chloroform/ether (mp-185°-7°).

EXAMPLE 12

Preparation of 1-(4-chlorophenyl)-1,4-dihydro-4-oxo-6-methylpyridazine-3-carboxylic acid and its sodium salt p-Chloroaniline (12.75 g) is dissolved in 40 ml of concentrated hydrochloric acid and cooled to 0°. A solution containing 7.6 g of sodium nitrite is added maintaining a temperature between 0° and 5°. The diazotized aniline is added under ice cooling to a previously prepared solution of 12.6 g 4-hydroxy-6-methyl-2-pyrone and 55 g sodium carbonate in 500 ml of water.

The resultant slurry is heated at reflux overnight. When complete reaction is not observed, the pH is adjusted to 12 and refluxing is continued. The dark solution is neutralized to pH 6–7 with acetic acid and treated with activated charcoal. The filtrate is acidified to pH 2 with concentrated hydrochloric acid under ice cooling to precipitate product. The acid is recrystallized from acetone/hexane yielding 10.5 g (39%) 1-(4-chlorophenyl)-1,4-dihydro-4-oxo-6-methylpyridazine-3-carboxylic acid (mp-229°–230° C.).

The acid (5.0 g) is converted to the sodium salt by treatment with 0.76 g sodium hydroxide in 200 ml of anhydrous methanol. The solvent is removed and the solid is washed with ether and dried in vacuo at 90° C.

Analysis calculated for $C_{12}H_8ClN_2ONa\cdot\frac{1}{2}H_2O$: C, 48.75; H, 3.07; N, 9.48; Cl, 11.99; Na, 7.78. Found: C, 48.11; H, 2.80; N, 9.24; Cl, 12.37; Na, 7.62.

EXAMPLE 14

Preparation of 1-Phenyl-1,4-dihydro-4-oxo-6-methylpyridazine-3-carboxylic acid

In 375 ml of water is suspended 11.8 g of 4-hydroxy-6-methyl-2-pyrone, and 9.95 g of anhydrous sodium carbonate is added to effect solution of the pyrone.

In a separate flask; 9.08 g of aniline is mixed with 37.5 ml of concentrated hydrochloric acid and 47 ml of water. The resulting solution is maintained at about 5° to 10° and a solution of 7.13 g of sodium nitrite in 24 ml of water is added. The resulting solution of phenyldiazonium chloride is added dropwise to the stirred pyrone solution, while maintaining a temperature of about 5° to 10°. The pH is maintained at about 8 to 9 by the addition of small amounts of sodium hydroxide solution.

After the addition is complete, the resulting hydrazone (18 g) is isolated by filtration and resuspended in 500 ml of concentrated hydrochloric acid. The mixture is refluxed for 2½ hours, and then cooled. The 1-phenyl-1,4-dihydro-4-oxo-6-methylpyridazine-3-carboxylic acid precipitates as brownish crystals which are recrystallized from water.

Yield—7.0 g; mp-173°.

EXAMPLE 16

Preparation of 1-(4-fluorophenyl)-5-bromo-1,4-dihydro-4-oxo-methyl pyridazine-3-carboxylic acid 1-(4-Fluorophenyl)-1,4-dihydro-4-oxo-6-methylpyridazine-3-carboxylic acid (1.5 g) is suspended in 100 ml of dry methanol, and 0.242 g of sodium hydroxide is added. To the solution is added dropwise 1.038 g of bromine dissolved in 50 ml of methanol. The solvent is removed leaving a white solid, which is taken up in dilute base and the solution acidified with hydrochloric acid. The resulting precipitate is filtered and recrystallized from chloroform/ether to yield 1.4 g of 1-(4-fluorophenyl)-5-bromo-1,4-dihydro-4-oxo-6-methylpyridazine-3-carboxylic acid. (mp-219°–20°).

EXAMPLE 20 n-Butyl 1-(4-bromophenyl) 1,4-dihydro-4-oxo-6-methylpyridazine-3-carboxylate

To an ice cooled solution of 50 ml n-butanol there is added dropwise 2.62 g (0.022 mol) of thionyl chloride (pot temperature maintained between −5° C. and 0° C.). The solution is stirred at 0° C. for 15 minutes and to it is added 6.18 g (0.02 mols) of 1-(4-bromophenyl)-1,4-dihydro-4-oxo-6-methylpyridazine-3-carboxylic acid (see Example 4). The suspension formed is stirred at room temperature for 3 days and to it there is added 150 ml of hexane. The suspension is stirred at room temperature for 2 days and is vacuum filtered. The filter cake (HCl salt of the desired product) is air dried and slurried in 150 ml of water for 3 hrs. The suspension is vacuum filtered to afford 5.25 g (72% yield ) of product, mp 85.5°–88° C.

EXAMPLE 21

Methyl 1-(4-iodophenyl)-1,4-dihydro-4-oxo-6-methylpyridazine-3-carboxylate

To 50 ml of methanol, cooled to −5°, there is added dropwise 2.62 g (0.022 mol) of thionyl chloride (pot temperature maintained between −5° C. and 0° C.). The solution is stirred at 0° C. for 15 min and to it there is added 7.12 g (0.02 mol) of 1-(4-iodophenyl)-1,4-dihydro-4-oxo-6-methylpyridazine-3-carboxylic acid. (See Example 3). The suspension formed is stirred at room temperature for 3 days and to it there is added 200 ml of water. The suspension that forms is stirred at room temperature for 2 days and is vacuum filtered. The filter cake is air dried to afford 4 g of crude product. The crude product is suspended in 25 ml of chloroform and filtered. The filtrate is concentrated in vacuo to afford 3.5 g (47% yield) of product, mp 185°–187° C.

EXAMPLE 22 n-Butyl 1-(4-iodophenyl)-1,4-dihydro-4-oxo-6-methylpyridazine-3-carboxylate

To 50 ml of n-butanol, cooled to −5° C., there is added dropwise 2.62 g (0.022 mol) of thionyl chloride. The solution is stirred at 0° C. for 15 minutes and to it there is added 7.12 g (0.02 mol) of 1-(4-iodophenyl)-1,4-dihydro-4-oxo-6-methylpyridazine-3-carboxylic acid. (See Example 3). The suspension formed is stirred at room temperature for 3 days and to it there is added 150 ml of hexane. The suspension is stirred at room temperature for 2 days and is vacuum filtered. The filter cake (HCl salt of the desired product) is air dried and slurried in 150 ml of water for 3 hrs. The suspension is vacuum filtered to afford 4.25 g (52% yield) of product, mp 134°–137° C.

EXAMPLE 23

Copper salt of 1-(4-chlorophenyl)-1,4-dihydro-4-oxo-3-carboxylic acid 6-methylpyridazin-4-one hexahydrate To a stirred suspension of 2.65 g (0.01 mol) 1-(4-chlorophenyl)-1,4-dihydro-4-oxo-6-methylpyridazine-3-carboxylic acid (see Example 12) in 50 ml of deionized water there is added 0.8 g (0.01 mol) of 50% aqueous sodium hydroxide. Within 10 minutes a pale yellow solution is formed and to it there is added dropwise a solution of 0.673 g (0.005 mol) cupric chloride in 10 ml of deionized water. The blue suspension formed is stirred at room temperature for 30 minutes and is vacuum filtered. The filter cake is washed with water and air dried to afford 2 g (58% yield) of product, mp 263°–265° C. decomp.

EXAMPLE 24

Methyl 1-(4-Methylthiophenyl)-1,4-dihydro-4-oxo-6-methylpyridazin carboxylate (A) (1-4-Methylthiophenyl)-1,4-dihydro-4-oxo-6-methylpyridazine-3-carboxylic acid To a mixture of 6.95 g (0.05 mol) p-methylthioaniline and 20 ml of 12 N hydrochloric acid in 25 ml of water, cooled to 5° C., there is added dropwise a solution of 3.8 g (0.055 mol) of sodium nitrite in 10 ml of water. The solution formed is added to an ice cooled solution of 6.3 g (0.05 mol) 4-hydroxy-6-methylpyran-2-one and 22 g (0.205 mol) of sodium carbonate in 125 ml of water. The suspension formed is stirred at 5° C. for 15 min, at room temperature for 2 hrs, and at reflux temperature for 3 hrs. The solution formed is allowed to stand at room temperature for 18 hrs. and is extracted with 3 (150 ml) portions of methylene dichloride. The aqueous solution is cooled to 5° C. and is acidified with 12 N hydrochloric acid. The suspension formed is stirred at room temperature for ½ hr and is vacuum filtered. Th filter cake is recrystallized from methanol to afford 6.14 g (45% yield) of product, mp 176°–179° C.

Elemental Analysis for $C_{13}H_{12}N_2O_3S$: calc: C 56.50, H 4.38, N 10.1, found: C 56.67, H 4.60, N 10.3.

(B) To 25 ml methanol, cooled to −5°, there is added dropwise 2.38 g (0.02 ml) of thionyl chloride. The solution formed is stirred at 0° C. for 15 minutes and to it there is added 3.04 g (0.01 mol) of 1-(4-methylthiophenyl)-1,4-dihydro-4-oxo-6-methylpyridazine-3-carboxylic acid. The suspension formed is stirred at 0° C. for 30 minutes and at room temperature for 18 hrs. The solution formed is concentrated in vacuo and the residue oil slurried in 100 ml of water for 2 hrs. The suspension is vacuum filtered and the filter cake air dried to afford 2.45 g of crude product. The crude product is recrystallized with toluene to afford 2 g (70% yield) of product, mp 157°–159° C.

EXAMPLE 25

Methyl 1-(4-Methylsulfonylphenyl)-1,4-dihydro-4-oxo-6-methylpyridazine-3-carboxylate To a suspension of 2.9 g (0.01 mol) Methyl 1-(4-methylthiophenyl)-1,4-dihydro-4-oxo-6-methylpyridazine-3-carboxylate (see Example 24) in 50 ml of glacial acetic acid, cooled to 5° C., there is added dropwise 3.4 g (0.02 mol) of 30% hydrogen peroxide (aqueous). The mixture is stirred at 5° C. for 1 hr. and at room temperature for 2 days. To the mixture there is added 200 ml of water and it is allowed to stir at room temperature for 1 hr. The suspension formed is vacuum filtered and the filter cake is recrystallized with methyl cellosolve to afford 1.15 g (36% yield) of product, mp 253°–257° decomp.

EXAMPLE 26

Sodium salt of
1-(4-Carbomethoxyphenyl)-1,4-dihydro-4-oxo-6-methylpyridazine-3-carboxylic acid (A)
3-(4-carbomethoxyphenylhydrazono)-4-oxo-6-methyl-pyr-2-one To a mixture of 3.78 g (0.025 mol) 4-carbomethoxy aniline and 10 ml of 12 N hydrochloric acid in 15 ml of water, cooled to 5° C., there is added dropwise a solution of 1.9 g (0.0275 mol) sodium nitrite in 5 ml of water. The solution formed is added to an ice cooled solution of 3.15 g (0.025 mol) 4-hydroxy-6-methyl pyr-2-one and 11 g (0.1025 mol) sodium carbonate in 65 ml of water. The suspension formed is stirred at 5° C. for 1 hr and at room temperature for 3 hrs. The suspension is vacuum filtered and the filter cake is air dried to afford 6.8 g (94.4% yield) of product, mp 230–240 decomp.

Elemental Analysis for $C_{14}H_{12}N_2O_5\frac{1}{2}H_2O$: Calc: C 56.56, H 4.41, N 9.43, Found: C 56.90, H 4.05, N 9.34.

(B)
1-(4-Carbomethoxyphenyl)-1,4-dihydro-4-oxo-6-methylpyridazine-3-carboxylic Acid To a suspension of 2.88 g (0.01 mol) 2-(4-carbomethoxyphenyl hydrazono)-4-oxo-6-methyl pyr-2-one in 25 ml of methanol there is added 12.5 ml of morpholine. The mixture is stirred at room temperature for 2 hrs and to it there is added 100 ml of water. The solution is cooled to 5° C. and is acidified with 12 N hydrochloric acid. The suspension formed is vacuum filtered and the filter cake is boiled in 25 ml of methanol, cooled to room temperature and vacuum filtered. The filter cake is air dried to afford 1.45 g (50% yield) of product, mp 217–218 decomp.

Elemental Analysis for $C_{14}H_{12}N_2O_5$: Calc: C 58.33, H 4.20, N 9.72, Found: C 58.38, H 4.42, N 9.67.

(C) Sodium salt of
1-(4-Carbomethoxyphenyl)-1,4-dihydro-4-oxo-6-methylpyridazine-3-carboxylic Acid To a suspension of 1.4 g (0.0049 mol) 1-(4-carbomethoxyphenyl)-1,4-dihydro-4-oxo-6-methyl pyridazine-3-carboxylic Acid in 50 ml of methanol there is added 0.39 g (0.0049 mol) of 50% aqueous sodium hydroxide. The fine suspension formed is concentrated in vacuo and the residue solid is slurried in 50 ml of ether for 15 minutes. The slurry is vacuum filtered and the filter cake dried in a vacuum desicator to afford 0.9 g (59%) of product, mp 300° C.

EXAMPLE 27

Sodium salt of
1-(4-Cyanophenyl)-1,4dihydro-4-oxo-6-methyl pyridazine-3-carboxylic Acid (A) 3-(p-cyanophenylhydrazono)-4-oxo-6-methyl pyr-2-one To a mixture of 5.9 g (0.05 mol) 4-aminobenzonitrile and 20 ml of 12 N hydrochloric acid in 25 ml of water, cooled to 5° C., there is added dropwise a solution of 3.8 g (0.055 mol) sodium nitrite in 10 ml of water. The solution formed is added to an ice cooled solution of 6.3 g (0.05 mol) 4-hydroxy-6-methyl pyr-2-one and 22 g (0.205 ml) of sodium carbonate in 125 ml of water. The suspension formed is stirred at 5° C. for 1 hr., at room temperature for 3 hrs. and is vacuum filtered. The filter cake is air dried to afford 12 g (94% yield) of product, mp 300° C.

Elemental Analysis for $C_{13}H_9N_3O_3\frac{1}{2}H_2O$: Calc: C 59.09, H 3.86, N 15.90, Found: C 58.85, H 3.53, N 15.98.

(B) 1-(4-Cyanophenyl)-1,4-dihydro-4-oxo-6-methyl pyridazine-3-carboxylic Acid

To a suspension of 5 g (0.019 mol) 3-(p-cyanophenyl-hydrazono-4-oxo-6-methyl pyr-2-one in 50 ml of methanol there is added 25 ml of morpholine (exothermic reaction). The solution formed is stirred at room temperature for ½ hr. and to it there is added 200 ml of water. The solution is cooled at 5° C. and is acidified with 12 N hydrochloric acid. The suspension formed is vacuum filtered and the filter cake air dried. The filter cake is boiled with 25 ml of methanol, cooled to room temperature and vacuum filtered. The filter cake is air dried to afford 2.4 g (48% yield) of product, mp 242°–244° C. decomp.

Elemental Analysis for $C_{13}H_9N_3O_3$: Calc: C 61.17, H 3.55, N 16.46, Found: C 61.46, H 3.76, N 16.62.

(C) Sodium salt of
1-(4-Cyanophenyl)-1,4-dihydro-4-oxo-6-methyl pyridazine-3-carboxylic Acid To a suspension of 2 g (0.00784 mol) 1-(4-cyano-phenyl)-1,4-dihydro-4-oxo-6-methyl pyridazine-3-carboxylic Acid in 50 ml of methanol there is added 0.63 g (0.00784 mol) of 50% aqueous sodium hydroxide. The solution formed is concentrated in vacuo and the residue slurried in 50 ml of ether for 15 min. The slurry is vacuum filtered and the filter cake is dried in a vacuum desicator to afford 1.9 g (81% yield) of product, mp 290° C. decomp.

EXAMPLE 28

Sodium salt of
1-(4-methylthiophenyl)-1,4-dihydro-4-oxo-6-methyl-pyridazine-3-carboxylic Acid (Na salt of precursor A in Example 24)

To a suspension of 2.76 g (0.01 mol) 1-(p-methylthio-phenyl)-3-carboxy-6-methyl pyridazine-3-carboxylic Acid in 20 ml of methanol there is added 0.79 g (0.01 mol) of 50% aqueous sodium hydroxide. The suspension is diluted with 80 ml of methanol and within 15 minutes a solution forms. The solution is concentrated in vacuo and the residue is slurried in 100 ml of ether. The slurry is vacuum filtered and the filter cake is air dried to afford 2.75 g (92% yield) of product, mp 310° C.

EXAMPLE 29

Methyl
1-(4-Chlorophenyl)-1,4-dihydro-4-oxo-5-n-propyl-6-methyl pyridazine-3-carboxylate and

EXAMPLE 30

Methyl
1-(4-Chlorophenyl)-1,4-dihydro-4-oxo-6-n-butylpyridazine-3-carboxylate (A) 4-Hydroxy-5-n-propyl-6-methyl-4-pyrone and 4-Hydroxy-6-n-butyl-4-pyrone To a suspension of 0.07 mol sodium amide in 200 ml of liquid ammonia, cooled to −33° C. and under a nitrogen blanket, there is added 4.0 g (0.0318 mol) of 4-hydroxy-6-methyl pyr-2-one. The green suspension formed is stirred at −33° C. for ½ hr. and to it there is added dropwise a solution of 3.94 g (0.032 mol) n-propyl bromide in 10 ml of ether. The mixture is stirred at −33° C. for ½ hr. and to it there is added 13 g of ammonium chloride. The mixture is allowed to warm to room temperature and the ammonia allowed to evaporate. During the ammonia evaporation 150 ml of ether is added to the mixture. Upon completion of the ammonia evaporation the mixture is cooled to 5° C. and 150 ml of ice water is added. The mixture is acidified with 12 N hydrochloric acid and the two phase solution is allowed to stand at room temperature overnight. The ethereal layer is isolated, dried over magnesium sulfate and concentrated in vacuo to afford 4.5 g (84% yield) of a mixture of products, yellow semi-solid.

(B) 1-(4-Chlorophenyl)-1,4-dihydro-4-oxo-6-n-butyl pyridazine-3-carboxylic Acid and 1-(4-Chlorophenyl)-1,4-dihydro-4-oxo-5-n-propyl-6-methylpyridazine-3-carboxylic Acid To an ice cooled solution (5° C.) of 3.19 g (0.025 mol) 4-chloroaniline and 10 ml of 12 N hydrochloric acid in 25 ml of water there is added dropwise a solution of 1.9 g (0.0275 mol) of sodium nitrite in 5 ml of water. The solution formed is added to an ice cooled solution of 4.2 g (0.025 mol) of the mixture (4-hydroxy-5-n-propyl-6-methyl-4-pyrone and 4-hydroxy-6-n-butyl-4-pyrone) and 11 g (0.104 mol) of sodium carbonate in 65 ml of water. The suspension formed is stirred at 5° C. for 1 hr., room temperature for 18 hrs. and at reflex temperature for 1½ hr. The mixture is cooled to room temperature and is extracted with 3 (250 ml) portions of methylene chloride. The aqueous layer is cooled to 5° C. and acidified with 12 N hydrochloric acid. The oil suspension is extracted with 3 (100 ml) portions of methylene dichloride. The extract is dried over magnesium sulfate and concentrated in vacuo to afford 3.2 g (42% yield) of a mixture of products, brown oil.

Elemental Analysis for $C_{15}H_{15}ClN_2O_3$: Calc: C 58.73, H 4.93, N 9.14, Found: C 58.58, H 5.03, N 8.94.

(C) Methyl 1-(4-Chlorophenyl)-1,4-dihydro-4-oxo-5-n-propyl-6-methylpyridazine-3-carboxylate and Methyl 1-(4-Chlorophenyl)-1,4-dihydro-4-oxo-6-n-butylpyridazine-3-carboxylate To 25 ml of methanol, cooled to −5° C., there is added 2.38 g (0.02 mol) of thionyl chloride. To the ice cooled solution is added 2.85 g (0.0093 mol) of the mixture of 1-(4-chlorophenyl)-1,4-dihydro-4-oxo-5-n-propyl-6-methyl pyridazine-3-carboxylic Acid and 1-(4-chlorophenyl)-1,4-dihydro-4-oxo-6-n-butyl pyridazine-3-carboxylic Acid dissolved in 25 ml of methanol. The solution is stirred at 0° C. for ½ hr. and at room temperature for 18 hrs. To the solution is added 250 ml of water and the oil suspension formed is stirred at room temperature for 1 hr. The suspension is extracted with 3 (100 ml) portions of methylene dichloride and the extract is dried over magnesium sulfate and concentrated in vacuo to afford 2.9 g of mixed products (oil). The mixture is separated using a silica gel dry column and ethyl acetate as eluent to afford 0.5 g (17% yield of example 30 (oil) and 0.5 g (17% yield) of example 29 (semi-solid).

EXAMPLE 31

Methyl 1-(4-Chlorophenyl)-1,4-dihydro-4-oxo-6-methyl pyridazine-3-carboxylate

To 100 ml of methanol, cooled to −5° C., there is added dropwise 11.9 g (0.1 mol) of thionyl chloride. Upon completion of the addition 13.23 g (0.05 mol) of 1-(4-chlorophenyl)-1,4-dihydro-4-oxo-6-methyl pyridazine-3-carboxylic Acid (see Example 12) is added. The suspension formed is vacuum filtered after stirring at room temperature for 3 hrs. to afford the product, mp 183°-193° C. decomp. Treatment of the product with water affords the Methyl 1-(4-chlorophenyl)-1,4-dihydro-4-oxo-6-methyl pyridazine-3-carboxylate.

EXAMPLE 32

Cyclohexyl 1-(4-chlorophenyl)-1,4-dihydro-4-oxo-6-methylpyridazine-3-carboxylate To an ice cooled suspension of 5.29 g (0.02 mol) 1-(4-chlorophenyl)-1,4-dihydro-4-oxo-6-methyl pyridazine-3-carboxylic Acid (see Example 12) and 2.02 g (0.02 mol) of triethylamine in 75 ml of toluene there is added 3.25 g (0.02 mol) of cyclohexyl chloroformate. The suspension formed is stirred at room temperature for 15 minutes and to it there is added 3.2 g (0.022 mol) of cyclohexanol in 50 ml of toluene. The mixture is stirred at room temperature for 38 hrs. and to it there is added 100 ml of water. The mixture is stirred at room temperature for 1 hr. and the toluene layer is isolated and poured into 600 ml of hexane. The suspension formed is stirred at room temperature for ½ hr. and is vacuum filtered. The filter cake is air dried to afford 4.5 g (65% yield) of product, mp 160°-162° C.

EXAMPLE 33

Dimethyl 1-(4-Chlorophenyl)-1,4-dihydro-4-oxo-6-methylpyridazine-3-carboxamide

To an ice cooled suspension of 2.65 g (0.01 mol) 1-(4-chlorophenyl)-1,4-dihydro-4-oxo-6-methyl pyridazine-3-carboxylic Acid (see Example 12) and 1.01 g (0.01 mol) of triethylamine in 50 ml of toluene there is added dropwise 1.09 g (0.01 mol) of ethyl chloroformate. The mixture is stirred at room temperature for 15 min. and is cooled to 5° C. To the mixture there is added 3.375 g (0.03 mol) of 40% dimethylamine (aqueous). The solution formed is stirred at room temperature for 18 hrs. and to it there is added 100 ml of water. The mixture is stirred at room temperature for 1 hr. and the aqueous layer is isolated. The aqueous layer is made basic with 50% sodium hydroxide and extracted with toluene. The toluene extract is dried over magnesium sulfate and concentrated in vacuo to afford 1.8 g of colorless tar. The tar is dissolved in 30 ml of methanol, saturated with anhydrous hydrogen chloride and concentrated in vacuo. The concentrate is slurried in 100 ml of ether for 1 hr. and vacuum filtered. The filter cake is air dried to afford 1.45 g (44% yield) of product, mp 125°-135° C. decomp.

EXAMPLE 34

1-(4-Carboxyphenyl)-1,4-dihydro-4-oxo-6-methyl-pyridazine-3-carboxylic Acid (A) 1-(4-Carboxymethyl)-1,4-dihydro-4-oxo-6-methyl pyridazine-3-carboxylic Acid To an ice cooled suspension of 11.33 g (0.075 mol) 4-carbomethoxy aniline in 40 ml of water there is added 30 ml of 12 N hydrochloric acid. The suspension is cooled to 0° C. and to it there is added 5.7 g (0.0825 mol) of sodium nitrite in 15 ml of water, dropwise. The solution formed is added to an ice cooled solution of 9.45 g (0.075 mol) 4-hydroxy-6-methyl pyr-2-one and 33 g (0.3075 mol) of sodium carbonate in 190 ml of water (considerable foaming is observed). The suspension is stirred at 5° C. for 1 hr., room temperature for 2 hrs. And refluxed for ½ hr. The solution formed is allowed to stand at room temperature for 18 hrs. and is extracted with 3 (200 ml) portions of methylene dichloride. The aqueous solution is acidified with 12 N hydrochloric acid at 10° C. and the suspension formed is vacuum filtered. The filter cake is boiled in 300 ml of methanol and vacuum filtered hot. The filter cake is air dried to afford 13.1 g (64% yield) of product, mp 290° C. decomp.

(B) 1-(4-Carboxyphenyl)-1,4-dihydro-4-oxo-6-methyl pyridazine-3-carboxylic Acid

To a suspension of 2.74 g (0.01 mol) 1-(4-carboxy phenyl)-1,4-dihydro-4-oxo-6-methyl pyridazine-3-carboxylic Acid in 50 ml of methanol there is added 0.8 g (0.01 mol) of 50% aqueous sodium hydroxide. The suspension is stirred at room temperature for 15 minutes and to it there is added another 0.8 g (0.01 mol) of 50% aqueous sodium hydroxide. The suspension is stirred at room temperature for ½ hr. and is vacuum filtered. The filter cake is washed with methanol and ether and dried in vacuum desicator to afford 2.85 g (85% yield) of product, mp 300° C.

EXAMPLE 35

Phenyl 1-(4-Chlorophenyl)-1,4-dihydro-4-oxo-6-methylpyridazine-3-carboxylate To an ice cooled suspension of 5.29 g (0.02 mol) 1-(4-chlorophenyl)-1,4-dihydro-4-oxo-6-methyl pyridazine-3-carboxylic Acid (see Example 12) and 2.02 g (0.02 mol) of triethylamine in 125 mol of toluene there is added dropwise 3.13 g (0.02 mol) of phenyl chloroformate. The suspension formed is stirred at room temperature for 15 minutes and to it there is added 1.88 g (0.02 mol) of phenol in 25 ml of toluene. The mixture is stirred at room temperature for 18 hrs. and to it there is added 100 ml of water. The suspension is stirred at room temperature for 2 hrs. and is poured into 800 ml of hexane. The suspension formed is stirred at room temperature for 3 hrs. and is vacuum filtered. The filter cake is slurried in 25 ml of toluene and is filtered. The filtrate is added to 150 ml of hexane and the suspension formed is stirred at room temperature for 2 hrs. The suspension is vacuum filtered and the filter cake air dried to afford 1.3 g (19% yield) of product, mp 140°-146° C.

EXAMPLE 36

Di-n-butyl 1-(p-Chlorophenyl)-1,4-dihydro-4-oxo-6-methyl pyridazine-3-carboxamide To an ice cooled suspension of 5.29 g (0.02 mol) 1-(4-chlorophenyl)-1,4-dihydro-4-oxo-6-methyl pyridazine-3-carboxylic Acid (see Example 12) and 2.02 g (0.02 mol) of triethylamine in 100 ml of toluene there is added dropwise 2.17 g (0.02 mol) of ethyl chlorofomate. The suspension formed is stirred at room temperature for 15 min. and is cooled to 5° C. To the suspension is added 2.59 g (0.02 mol) di-n-butylamine and the mixture is stirred at room temperature for 18 hrs. To the mixture is added 100 ml of water and the suspension formed is stirred at room temperature for 1 hr. The toluene layer is isolated, dried over magnesium sulfate and concentrated in vacuo. The residue oil is dissolved in 25 ml of ether and to it there is added 25 ml of hexane. The mixture is allowed to stand at room temperature for 30 minutes and is vacuum filtered. The filter cake is washed with hexane and air dried to afford 5.5 g (73% yield) of product, mp 101°-105° C.

EXAMPLE 37

Benzyl 1-(4-Chlorophenyl)-1,4-dihydro-4-oxo-6-methyl pyridazine-3-carboxylate To 25 ml of benzyl alcohol, cooled to −5° C., there is added dropwise 2.62 g (0.022 mol) of thionyl chloride. The solution is stirred at −5° C. for 5 minutes and to it there is added 5.29 g (0.02 mol) of 1-(4-chlorophenyl)-1,4-dihydro-4-oxo-6-methyl pyridazine-3-carboxylic Acid (see Example 12) and 25 ml of benzyl alcohol. The suspension formed is stirred at 0° C. for ½ hr. and room temperature for 18 hrs. To the suspension there is added 100 ml of toluene and 100 ml of hexane. The suspension is stirred at room temperature for ½ hr. and is vacuum filtered. The filter cake (the HCl salt of the product), mp 148-162, is slurried in 100 ml of water for 1 hr. and is vacuum filtered. The filter cake is recrystallized with toluene to afford 4 g (56.4% yield) of product, mp 164°-166° C.

EXAMPLE 38

Methoxyethyl 1-(4-Chlorophenyl)-6-methyl pyridazine-3-carboxylate

To 25 ml of methyl cellosolve, cooled to −5° C., there is added dropwise 2.62 g (0.022 mol) of thionyl chloride. The solution is stirred at −5° C. for 5 minutes and to it there is added 5.29 g (0.02 mol) of 1-(4-chlorophenyl)-1,4-dihydro-4-oxo-6-methyl pyridazine-3-carboxylic Acid (see Example 12) and 25 ml of methyl cellosolve. The suspension is stirred at 0° C. for ½ hr. and at room temperature for 2 days. To the suspension there is added 150 ml of water and the mixture is stirred at room temperature for 1 hr. The suspension is vacuum filtered and the filter cake is recrystallized with toluene to afford 4.55 g (70.5% yield) of product, mp 130°-133° C.

EXAMPLE 39

Cyclohexy Methyl 1-(4-Chlorophenyl)-1,4-dihydro-4-oxo-6-methyl pyridazine-3-carboxylate To an ice cooled suspension of 5.29 g (0.02 mol) 1-(4-chlorophenyl)-1,4-dihydro-4-oxo-6-methyl pyridazine- 3-carboxylic Acid (see Example 12) and 2.02 g (0.02 mol) of triethylamine in 75 ml of toluene there is added 3.5 g (0.02 mol) of cyclohexylmethyl chloroformate. The mixture is stirred at room temperature for 15 min. and to it there is added 2,5 g (0.022 mol) of cyclohexylmethanol. The mixture is stirred at room temperature for 18 hrs. and to it there is added 100 ml of water. The suspension is stirred at room temperature for 1 hr. and the toluene layer is isolated and poured into 600 ml of hexane. The suspension formed is stirred at room temperature for 1 hr. and is vacuum filtered. The filter cake is air dried to afford 5 g (69.3% yield) of product, mp 125°–127° C.

EXAMPLE 40

3-Bromopropyl 1-(4-Chlorophenyl)-1,4-dihydro-4-oxo-6- methyl pyridazine-3-carboxylate To an ice cooled suspension of 5.29 g (0.02 mol) 1-(4-chlorophenyl)-1,4-dihydro-4-oxo-6-methyl pyridazine-3-carboxylic Acid (see Example 12) and 2.02 g (0.02 mol) of triethylamine in 75 ml of toluene there is added 4.03 g (0.02 mol) of 3-bromopropyl chloroformate. The suspension formed is stirred at room temperature for 20 min. and to it there is added 3.06 g (0.022 mol) of 3-bromopropanol in 50 ml of toluene. The mixture is stirred at room temperature for 5 days and to it there is added 100 ml of water. The mixture is stirred at room temperature for 1 hr. and the toluene layer is isolated and poured into 500 ml of hexane. The suspension formed is vacuum filtered and the filter cake is air dried to afford 4.3 g (56% yield) of product, mp 87°–92° C.

EXAMPLE 41

Ethyl 1-(4-Chlorophenyl)-1,4-dihydro-4-oxo-6-methyl pyridazine-3-carboxythiolate To an ice cooled suspension of 5.29 g (0.02 mol) of 1-(4-chlorophenyl)-1,4-dihydro-4-oxo-6-methyl pyridazine-3-carboxylic Acid (see Example 12) and 2.02 g (0.02 mol of triethylamine in 75 ml of toluene there is added dropwise 2.49 g (0.02 mol) of ethyl chlorothioformate. The suspension is stirred at room temperature for 15 min. and to it there is added 1.37 g (0.022 mol) of ethanethiol in 50 ml of toluene. The mixture is stirred at room temperature for 2 days and to it there is added 100 ml of water. The toluene solution is isolated and poured into 600 ml of hexane. The suspension formed is vacuum filtered and the filter cake is air dried to afford 1.35 g (22% yield) of product, mp 117°–119° C.

EXAMPLE 42

Methyl 1-(4-Chlorophenyl)-1,4-dihydro-4-thioxo-6-methyl pyridazine-3-carboxylate A mixture of 2.79 g of (0.01 mol) Methyl 1-(4-chlorophenyl)-1,4-dihydro-4-oxo-6-methyl pyridazine-3-carboxylate (see Example 31) and 2.89 g (0.013 mol) of phosphorous pentasulfide in 100 ml of toluene is refluxed and stirred for 3 hrs. To the black suspension formed is added 100 ml of water and the mixture is made basic with 50% aqueous sodium hydroxide (at room temperature). The toluene layer is isolated, dried over magnesium sulfate and concentrated in vacuo to afford 0.65 g of product, mp 142°–150° C. decomp. The product is boiled in 200 ml of methyl cyclohexane and filtered hot. The insoluble material is labeled A (yield 0.15 g, mp 154°–156° C. decomp.) and the crystallized material is labelled B (yield 0.3 g, mp 156.5°–158° C. decomp.). Both A and B products are combined.

EXAMPLE 45

Carbomethoxy methyl 1-(4-Chlorophenyl)-1,4-dihydro-4-oxo-6-pyridazine-3-carboxamide To an ice cooled suspension of 7.95 g (0.03 mol) 1-(4-chlorophenyl)-1,4-dihydro-4-oxo-6-methylpyridazine-3-carboxylic acid and 9.18 g (0.09 mol) of triethylamine in 150 ml of toluene there is added dropwise 3.27 g (0.03 mol) of ethyl chloroformate. The mixture is stirred at 5° C. for 20 min. and to it there is added a solution of 3.75 g (0.03 mol) glycine methyl ester hydrochloride and 3.06 g (0.03 mol) of triethylamine in 9 ml of water. The mixture is stirred at 5° C. for 1 hr. and at room temperature for 2 hrs. To the mixture there is added 150 ml of water and it is stirred at room temperature for 1 hr. The suspension is vacuum filtered and the filter cake is air dried to afford 4.15 g (41% yield) of product, mp 166–168.

EXAMPLE 46

Carboxy methyl 1-(4-Chlorophenyl)-1,4-dihydro-4-oxo-6-methylpyridazine-3-carboxamide To a suspension of 2.0 g (0.006 mol) Carboxy methyl 1-(4-chlorophenyl)-1,4-dihydro-4-oxo-6-methylpyridazine-3-carboxamide in 50 ml of water there is added 0.8 g (0.006 mol) of 50% aqueous sodium hydroxide. The mixture is heated to reflux over a period of 10 min., maintained at reflux temperature for 3 min. and allowed to cool to room temperature over a period of 1 hr. The solution is cooled to 5° C. and acidified with 12 N hydrochloric acid. The suspension formed is vacuum filtered and the filter cake is air dried to afford 1.3 g (67% yield) of product, mp 296–298 decomp.

EXAMPLE 47

1-(4-Chlorophenyl)-1,4-dihydro-4-oxo-6-phenyl pyridazine-3-carboxylic acid: Sodium salt To an ice cooled solution of 3.19 g (0.025 mol) p-chloroaniline and 10 ml of 12 N hydrochloric acid in 25 ml of water there is added dropwise a solution of 1.9 g (0.0275 mol) sodium nitrite in 5 ml of water. The solution formed is added to an ice cooled mixture of 4.7 g (0.025 mol) 4-hydroxy-6-phenyl pyr-2-one and 11 g of sodium carbonate in 65 ml of water. The thick orange suspension formed is stirred at 5° C. for 1 hr., room temperature for 18 hrs., stirred and refluxed for 4 hrs. and stirred at room temperature for 18 hrs. The suspension is vacuum filtered to afford 6.25 g of hydrazone, mp 300° C.

The hydrazone (3.0 g; 0.0092 mol) is suspended in 50 ml of 12 N hydrochloric acid and is refluxed and stirred for 1 hr., stirred at room temperature for 18 hrs. and refluxed and stirred for 2 hrs. The mixture is cooled to room temperature and diluted with 200 ml of water. The mixture is vacuum filtered and the filter cake is air dried to afford 2.5 g (83% yield) of the 1-(4-chlorophenyl)-1,4-dihydro-4-oxo-6-phenyl pyridazine-3-carboxylic acid, mp 229–234 decomp.

To a suspension of 1.35 g (0.00413 mol) of the 1-(4-chlorophenyl)-1,4-dihydro-4-oxo-6-methylpyridazine-3-carboxylic acid 50 ml of methanol there is added 0.33 g (0.00413 mol) of 50% aqueous sodium hydroxide. The mixture is stirred at room temperature for 2 days, refluxed for 5 min. and stirred at room temperature for 3 days. The mixture is vacuum filtered and the filtrate is concentrated in vacuo. The residue of the concentrated filtrate is stirred in 50 ml of diethyl ether and is vacuum filtered. The filter cake is air dried to afford 0.75 g (52% yield) of product, mp 206–225 decomp.

EXAMPLE 48

Sodium salt of 1-(4-Chlorophenyl)-1,4-dihydro-4-oxo-5,6-cyclohexa[b]-pyridazine-3-carboxylic Acid To an ice cooled solution of 2.12 g (0.0166 mol) 4-chloroaniline and 6.6 ml of 12 N hydrochloric acid in 10 ml of water there is added a solution of 1.26 g (0.0183 mol) sodium nitrite in 3 ml of water. The solution formed is added to an ice cooled solution of 2.75 g (0.0166 ml) 4-hydroxy-5,6-cyclohexa[b]-pyr-2-one and 7.5 g sodium carbonate in 50 ml of water. The thick yellow suspension formed is stirred at 0° C. for 1 hr., room temperature for 2 hrs. and refluxed for 2½ hrs. The solution formed is stirred at room temperature for 18 hrs. and is extracted with 3 (100 ml) portions of methylene dichloride. The aqueous solution is acidified with 12 N hydrochloric acid and the suspension formed is vacuum filtered. The filter cake is air dried to afford 3.9 g (77% yield, of 1-(4-chlorophenyl-1,4-dihydro-4-oxo-5,6-cyclohexa[b]-pyridazine-3-carboxylic acid, mp 209–212 decomp.

To a suspension of 2.0 g (0.0066 mol) of the 1-(4-chlorophenyl)-1,4-dihydro-4-oxo-5,6-cyclohexa[b]-pyridazine-3-carboxylic acid in 25 ml of methanol there is added 0.525 g (0.0066 mol) of 50% aqueous sodium hydroxide. The mixture is stirred at room temperature for 15 min. and the thick suspension formed is diluted with 25 ml of methanol. The suspension is stirred at room temperature for 1 hr. and is concentrated in vacuo to a volume of 5 ml. The residue is slurried in 50 ml of diethyl ether and vacuum filtered (filter cake is unchanged free acid). The filtrate is concentrated in vacuo to afford 0.85 g of product, mp 206–220 slow decomp.

EXAMPLE 53

Potassium salt of Hydroxy 1-(4-chlorophenyl)-1,4-dihydro-4-oxo-methylpyridazine-3-carboxamate A suspension of 1.5 g (0.0216 mol) hydroxylamine hydrochloride in 25 ml of anhydrous methanol is heated to reflux temperature and the solution formed is cooled 0° C. To the solution there is added a solution of 2.1 g (0.0324 mol) potassium hydroxide pellets (86%) dissolved in 20 ml of anhydrous methanol. The suspension formed is stirred at 0° C. for 5 min. and to it there is added 3.0 g. (0.0108 mol) of methyl 1-(4-chlorophenyl)-1,4-dihydro-4-oxo-6-methyl pyridazine-3-carboxylate. The suspension formed is vacuum filtered and the filtrate is allowed to stand at room temperature, when anhydrous conditions, for 5 days. The concentrate is slurried in anhydrous diethyl ether for 18 hours. The slurry is vacuum filtered and the filter cake dried to afford 2.4 g (60% yield) of product, np 197° vigorous decomp.

Elemental Analysis for $C_{12}ClKN_3O_3.3(H_2O)$: Calc: C 38.76; H 4.07; N 11.30, Found: C 38.31; H 2.79; N 11.58.

Table I lists typical compounds of the invention and their melting point and elemental analysis which have been prepared utilizing the procedures described above.

TABLE I

1-Aryl-1,4-dihydro-4-oxo(thio)-pyridazines

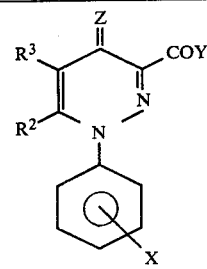

| Example No. | R³ | R² | Z | X | Y |
|---|---|---|---|---|---|
| 1 | H | CH₃ | O | 3-F | OH |
| 2 | H | CH₃ | O | 4-CH₃ 3-Cl | OH |
| 3 | H | CH₃ | O | 4-I | OH |
| 4 | H | CH₃ | O | 4-Br | OH |
| 5 | H | CH₃ | O | 4-CF₃ | OH |
| 6 | H | CH₃ | O | 4-NO₂ | OH |
| 7 | H | CH₃ | O | 4-CH₃ | OH |
| 8 | H | CH₃ | O | 2,3-benzo-4-Cl | OH |
| 9 | H | CH₃ | O | 4-OCH₃ | OH |
| 10 | H | CH₃ | O | 4-F | OH |
| 11 | H | CH₃ | O | 3,4-diCl | OH |
| 12 | H | CH₃ | O | 4-Cl | OH |
| 13 | H | CH₃ | O | 3-Cl | OH |
| 14 | H | CH₃ | O | H | OH |
| 15 | Br | CH₃ | O | 4-CH₃ | OH |
| 16 | Br | CH₃ | O | 4-F | OH |
| 17 | Br | CH₃ | O | 4-Br | OH |
| 18 | Br | CH₃ | O | H | OH |
| 19 | Cl | CH₃ | O | 4-Br | OH |
| 20 | H | CH₃ | O | 4-Br | O—n-Bu |
| 21 | H | CH₃ | O | 4-I | OCH₃ |
| 22 | H | CH₃ | O | 4-I | O—n-Bu |
| 23 | H | CH₃ | O | 4-Cl | O—(½Cu++) |
| 24 | H | CH₃ | O | 4-CH₃S | OCH₃ |
| 25 | H | CH₃ | O | 4-CH₃SO₂ | OCH₃ |
| 26 | H | CH₃ | O | 4-CH₃CO₂ | ONa |
| 27 | H | CH₃ | O | 4-CN | ONa |
| 28 | H | CH₃ | O | 4-CH₃S | ONa |
| 29 | n-C₃H₇ | CH₃ | O | 4-Cl | OCH₃ |
| 30 | H | n-C₄H₉ | O | 4-Cl | OCH₃ |
| 31 | H | CH₃ | O | 4-Cl | OCH₃ |
| 32 | H | CH₃ | O | 4-Cl | O—C₆H₁₁ |
| 33 | H | CH₃ | O | 4-Cl | N(CH₃)₂ |
| 34 | H | CH₃ | O | 4-COONa | ONa |
| 35 | H | CH₃ | O | 4-Cl | O—C₆H₅ |
| 36 | H | CH₃ | O | 4-Cl | N—(Bu)₂ |
| 37 | H | CH₃ | O | 4-Cl | OCH₂—C₆H₅ |
| 38 | H | CH₃ | O | 4-Cl | OCH₂CH₂OCH₃ |
| 39 | H | CH₃ | O | 4-Cl | OCH₂C₆H₁₁ |
| 40 | H | CH₃ | O | 4-Cl | OCH₂CH₂CH₂Br |
| 41 | H | CH₃ | O | 4-Cl | SCH₂CH₃ |
| 42 | H | CH₃ | S | 4-Cl | OCH₃ |
| 43 | H | CH₃ | O | 4-Cl | OCH₃ |
| 44 | H | CH₃ | O | 4-Cl | OC₂H₅ |
| 45 | H | CH₃ | O | 4-Cl | NHCH₂CO₂CH₃ |
| 46 | H | CH₃ | O | 4-Cl | NHCH₂CO₂H |
| 47 | H | C₆H₅ | O | 4-Cl | ONa |
| 48 | —(CH₂)₄— | | O | 4-Cl | OCH₃ |
| 49 | H | C₂H₅ | O | 4-Cl | OCH₃ |
| 50 | H | C₂H₅ | O | 4-Cl | ONa |
| 51 | CH₃ | C₂H₅ | O | 4-Cl | ONa |
| 52 | CH₃ | C₂H₅ | O | H | ONa |
| 53 | H | CH₃ | O | 4-Cl | NHOK |

TABLE II

| Example No. | m.p. (°C.) | | % C | % H | % N | % Hal |
|---|---|---|---|---|---|---|
| 1 | 213-5 | Calc. | 58.06 | 3.65 | 11.29 | 7.65 |
|   |       | Found | 58.07 | 3.60 | 11.33 | 7.68 |
| 2 | 202-3 |       | 56.22 | 3.63 | 10.09 | 12.77 |
|   |       |       | 55.92 | 3.64 | 10.90 | 13.36 |
| 3 | 241-2 |       | 40.47 | 2.55 | 7.87 | 35.64 |
|   |       |       | 41.20 | 2.46 | 8.05 | 35.67 |
| 4 | 243   | Calc. | 46.62 | 2.93 | 9.06 | 25.85 |
|   |       | Found | 47.45 | 3.14 | 9.26 | 25.64 |
| 5 | 234-5 |       | 52.35 | 3.04 | 9.40 | 19.11 |
|   |       |       | 51.99 | 2.97 | 9.13 | 18.94 |
| 6 | 244-5 |       | 52.37 | 3.30 | 15.27 | — |
|   |       |       | 52.76 | 3.33 | 15.69 | — |
| 7 | 162-3 |       | 63.92 | 4.95 | 11.47 | — |
|   |       |       | 63.66 | 4.89 | 11.52 | — |
| 8 | 218-20 |      | 61.06 | 3.52 | 8.90 | 11.27 |
|   |       |       | 61.07 | 3.42 | 8.86 | 11.00 |
| 9 | 169-70 |      | 59.94 | 4.64 | 10.77 | — |
|   |       |       | 60.14 | 4.62 | 10.82 | — |
| 10 | 185-7 |      | 58.06 | 3.65 | 11.29 | 7.65 |
|   |       |       | 58.73 | 3.64 | 11.74 | 7.47 |
| 11 | 220-2 |      | 48.18 | 2.69 | 9.37 | 23.71 |
|   |       |       | 48.03 | 2.73 | 9.21 | 23.96 |
| 12 | 229-30 |     | 54.45 | 3.43 | 10.59 | 13.39 |
|   |       |       | 54.49 | 3.44 | 10.44 | 13.59 |
| 13 | 192-3 |      | — | — | — | — |
|   |       |       | — | — | — | — |
| 14 | 183-185 |    | 62.60 | 4.38 | 12.17 | — |
|   |       |       | 62.91 | 4.35 | 12.89 | — |
| 15 | 241 |        | 48.31 | 3.43 | 8.67 | 24.73 |
|   |       |       | 49.37 | 3.59 | 9.25 | 23.65 |
| 16 | 219-20 |     | 44.06 | 2.46 | 8.57 | 24.43[a] |
|   |       |       | 44.50 | 2.52 | 9.00 | 24.26 |
| 17 | 250 |        | 37.14 | 2.08 | 7.22 | 41.19 |
|   |       |       | 36.78 | 1.98 | 7.35 | 40.83 |
| 18 | 220 |        | 46.62 | 2.93 | 9.06 | 25.85 |
|   |       |       | 46.68 | 2.88 | 9.25 | 25.62 |
| 19 | 255-9 |      | 41.95 | 2.35 | 8.16 | 23.26[b] |
|   |       |       | 41.65 | 2.31 | 7.74 | 23.17 |
| 20 | 85.5-88 |    | 52.61 | 4.69 | 7.67 |  |
|   |       |       | 52.25 | 4.70 | 7.90 |  |
| 21 | 186-189 |    | 42.18 | 3.00 | 7.57 |  |
|   |       |       | 41.95 | 2.91 | 7.16 |  |
| 22 | 134-137 |    | 46.61 | 4.16 | 6.80 |  |
|   |       |       | 46.84 | 4.26 | 6.95 |  |
| 23 | 263-265 |    | 41.24 | 4.04 | 8.02 | 10.15[c] |
|   |       |       | 39.55 | 3.40 | 7.62 | 9.35 |
| 24 | 157-159 |    | 57.91 | 4.86 | 9.65 |  |
|   |       |       | 57.98 | 4.88 | 9.66 |  |
| 25 | 253-257 |    | 52.26 | 4.38 | 8.69 |  |
|   |       |       | 52.09 | 4.57 | 9.10 |  |
| 26 | >300 |       | 51.22 | 3.99 | 8.54[d] |  |
|   |       |       | 51.32 | 3.73 | 8.68 |  |
| 27 | 290 |        | 52.09 | 3.53 | 14.02[e] |  |
|   |       |       | 52.12 | 3.16 | 14.03 |  |
| 28 | >310 |       | — | — | — |  |
|   |       |       | — | — | — |  |
| 29 | Semi-Solid | Calc. | 59.90 | 5.34 | 8.74 |  |
|   |       | Found | 60.13 | 5.45 | 8.57 |  |
| 30 | oil |        | 59.90 | 5.34 | 8.74 |  |
|   |       |       | 59.85 | 5.61 | 9.11 |  |
| 31 | 183-193 |    | 49.54 | 3.84 | 8.89[f] |  |
|   |       |       | 50.12 | 3.69 | 9.29 |  |
| 32 |       |       | 62.33 | 5.52 | 8.08 |  |
|   |       |       | 62.45 | 5.72 | 8.45 |  |
| 33 | 125-135 |    | 49.86 | 4.78 | 12.46[g] |  |
|   |       |       | 49.54 | 4.71 | 13.05 |  |
| 34 | >300 |       | 46.44 | 3.00 | 8.33[h] |  |
|   |       |       | 46.41 | 3.15 | 8.32 |  |
| 35 | 140-146 |    | 63.44 | 3.84 | 8.22 |  |
|   |       |       | 62.85 | 3.99 | 8.80 |  |
| 36 | 101-105 |    | 63.90 | 6.97 | 11.18 |  |
|   |       |       | 63.69 | 6.89 | 11.67 |  |
| 37 | 164-166 |    | 64.32 | 4.26 | 7.90 |  |
|   |       |       | 64.39 | 4.27 | 8.22 |  |
| 38 | 130-133 |    | 55.82 | 4.68 | 8.68 |  |
|   |       |       | 55.86 | 4.50 | 8.41 |  |
| 39 | 125-127 |    | 63.24 | 5.87 | 7.77 |  |
|   |       |       | 63.44 | 5.97 | 7.48 |  |
| 40 | 87-92 |      | 46.71 | 3.66 | 7.27 |  |
|   |       |       | 47.23 | 3.75 | 6.93 |  |
| 41 | 117-119 |    | 54.45 | 4.24 | 9.07[j] |  |
|   |       |       | 55.18 | 4.31 | 8.72 |  |
| 42 | 154-156 |    | 52.97 | 3.76 | 9.51[j] |  |
|   |       |       | 52.45 | 3.89 | 9.48 |  |
| 43 | 200-202 |    | 56.02 | 3.98 | 10.05 | 12.72 |
|   |       |       | 56.15 | 4.06 | 10.10 | 12.71 |
| 44 | 143 |        | 57.44 | 4.48 | 9.57 | 12.11[k] |
|   |       |       | 57.37 | 4.51 | 9.56 | 12.06 |
| 45 | 166-168 |    | 53.66 | 4.20 | 12.52 |  |
|   |       |       | 53.95 | 4.27 | 12.61 |  |
| 46 | 296-298 |    | 52.26 | 3.76 | 13.06 |  |
|   |       |       | 52.12 | 3.81 | 13.38 |  |
| 47 | 206-225 |    | 62.49 | 3.39 | 8.58[l] |  |
|   |       |       | 62.73 | 3.40 | 8.62 |  |
| 48 | 206-220 |    | 59.12 | 4.30 | 9.20 |  |
|   |       |       | 59.02 | 4.26 | 9.48 |  |
| 49 | 110-114 |    | 57.44 | 4.48 | 9.57 |  |
|   |       |       | 57.20 | 4.34 | 9.60 |  |
| 50 |       |       | 48.99 | 3.80 | 8.79[m] |  |
|   |       |       | 48.22 | 3.56 | 9.22 |  |
| 51 | 165 |        | 50.53 | 4.24 | 8.42[n] |  |
|   |       |       | 50.39 | 3.86 | 8.41 |  |
| 52 | 135 |        | 56.37 | 5.07 | 4.39[o] |  |
|   |       |       | 57.42 | 4.86 | 9.58 |  |

[a] % Br; % F: calc. 5.81; found 5.83
[b] % Br; % Cl; calc. 10.37; found 9.91
[c] % Cl; % Cu: calc. 9.09; found 10.60; % H O: calc. 15.47; found 15.96
[d] % Na: calc. 7.01; found 8.19
[e] analysis for monohydrate
[f] analysis for hydrochloride salt
[g] analysis for hydrochloride salt
[h] % Na: calc. 13.68; found 13.2
[i] % S: calc. 10.38; found 10.3
[j] % S: calc. 10.88; found 12.25
[k] % Cl:
[l] analysis for free acid
[m] % Na: calc. 7.22; found 7.40; % H₂O: calc. 5.65; found 4.74 (monohydrate)
[n] % Na: calc. 6.91; found 6.1; % H₂O: calc. 5.42; found 4.31 (monohydrate)
[o] % Na: calc. 7.71; found 7.3; % H₂O: calc. 6.04; found 5.73 (monohydrate)

The compounds of the invention are particularly useful as chemical hybridization agents in cereal crops, such as wheat, barley, corn, rice, sorghum, millets, teff, oats, rye and the like and forage crops. When used as chemical hybridization agents, the compounds effectively induce a high degree of selective male sterility, that is without also inducing significant female sterility, in the treated plants and without causing significant growth inhibition of the treated plants. As used herein, the term male sterility is evidenced by a lack of seed set, in which the male flower parts are unable to cause pollination. The compounds of the invention also cause other plant growth regulatory responses, such as for example, control of flowering, control of fruiting and inhibition of seed formation in non-cereal species, and other related growth regulatory responses.

When used as plant growth regulators, the compounds of the invention are applied in an amount which will be sufficient to effect the desired plant response without causing undesirable or phytotoxic response. For example, when the compounds of the invention are used as chemical hybridization agents, they are generally applied to the crops to be treated at a rate of about 1/32 to about 20 pounds per acre and preferably about ⅛ to about 10 pounds per acre. The rate of application will vary depending on the crop being treated, the compound being used for treatment, and related factors.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A preferred method of applying a compound of the invention as a chemical hybridization agent is by foliar application. When this method is employed, selective male sterility is most effectively induced when the compound is applied between flower initiation and meiosis. The compounds of the inventions may also be applied as a seed treatment by soaking the seed in a liquid formulation containing the active compound or by coating the seed with the compound. In seed treatment applications, the compounds of the invention will generally be applied at a rate of about 1/16 to 10 pounds per hundred weight of seed. The compounds of the invention are also effective when applied to the soil or to the water surface in rice crops.

The compounds of the invention can be used as plant growth regulators either individually or in mixtures. For example, they can be used in combination with other plant growth regulators, such as auxins, gibberellins, ethylene-releasing agents such as ethephon, pyridones, cytokinins, maleic hydrazide, succinic acid 2,2-dimethyl-hydrazide, choline and its salts, (2-chloroethyl)trimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts, and N-dimethylamine-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no significant detrimental effect on the soil, equipment, crops, or argonomic environment. Mixtures of the compounds of the invention may also be used in any of these formulations. The compositions of the invention can be either solid or liquid formulations as wettable powders, emulsifiable concentrates, dusts, granular formulations, aerosols, or flowable emulsion concentrates. In such formulations, the compounds are extended with a liquid or solid carrier and, when desired suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent or surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually about 10% to 60% by weight and in flowable emulsion concentrates of usually about 10% to 60% by weight and in flowable emulsion concentrates this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent may generally constitute about 0.5% to about 3% by weight of the composition, and a wetting agent may generally constitute from about 0.1% to about 5% weight of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% by weight use concentration.

Granular formulations can be prepared by impregnating a solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% by weight of the granular formulation.

Salts of the compounds of the invention can be formulated and applied as aqueous solutions. The salts will typically comprise about 0.05 to about 50% by weight, preferably about 0.1% to about 10%, of the solution. These compositions can also be further diluted with water if desired prior to actual application. In some applications, the activity of these compositions can be enhanced by incorporating into the compositions an adjuvant such as glycerin, methylethylcellulose, hydroxyethylcellulose, polyoxyethylenesorbitan monooleate, polypropylene glycol, polyacrylic acid, polyethylene sodium malate, polyethylene oxide, or the like. The adjuvant will generally comprise about 0.1 to about 5% by weight, preferably about 0.5 to about 2%, of the composition. Such compositions can also optionally include an agronomically-acceptable surfactant.

The compounds of the invention can be applied as sprays by methods commonly employed, such as conventional hydraulic sprays, aerial sprays, and dusts. For low-volume applications as solution of the compound is usually used. The dilution and volume of application will usually depend upon such factors as the type of equipment employed, the method of application, the area to be treated and the type and stage of development of the crop being treated.

The following example will further illustrate the growth regulatory activity of the compounds of the invention but is not intended to limit the invention in any way.

EXAMPLE 43

Chemical Hybridization Activity

The following procedures are used to evaluate the activity of the compounds of the invention for inducing male sterility of cereals.

An awned variety (Fielder) and an awnless variety (Mayo-64) of spring wheat are planted at the rate of 6 to 8 seeds pr 6" not containing a sterile medium of 3 parts soil and 1 part humus. The plants are grown under short-day (9 hour) conditions for the first 4 weeks to obtain good vegetative growth before flower initiation. The plants are then moved to long-day (16 hour) conditions which are provided by high intensity lights in the greenhouse. The plants are fertilized at 2, 4, and 8 weeks after planting with a water soluble fertilizer (16-25-16) at the rate of 1 tsp/gal of water, and are frequently sprayed with an appropriate insecticide, such as Isotox$^R$, for aphid control and dusted with sulfur for powdery mildew control.

Test compounds are foliarly applied to the awned female plants when these plants reach the flag leaf emergence state (stage 8 on Feekes' scale). All compounds are applied in a carrier volume of 50 gal/A containing a surfactant, such as Triton$^R$ X-100, at the rate of 2 oz/50 gal.

After spike emergence but before anthesis, 4 to 6 spikes per pot are bagged to prevent outcrossing. At the first signs of flower opening, two spikes per pot are cross pollinated, using the approach method, with the awnless male parent. As soon as the seeds became plainly visible, spike length is measured and seeds per spikelet counted in both bagged and crossed spikes. Male sterility can then be calculated as percent inhibition of seed set in bagged spikes of treated plants, and female fertility in crossed spikes can be calculated as percent of control seed set. After maturity the seed on crossed spikes are planted for determination of percent hybridization.

Percent sterility, percent fertility, and percent spike length inhibition are calculated from the following formulas:

$$\text{(a) \% Sterility} = \frac{S_c - S_t}{S_c} \times 100$$

$S_c$ = seeds/spikelet in bagged spikes of control plants
$S_t$ = seeds/spikelet in bagged spikes of treated plants (b) % Fertility = $(F_t/F_c) \times 100$
$F_t$ = seeds/spikelets in approach crossed spikes of treated plants
$F_c$ = seeds/spikelet in unbagged spikes of control plants $$\text{(c) \% Spike inhibition} = \frac{H_c - H_t}{H_c} \times 100$$

$H_c$ = Spike length of control plants
$H_t$ = Spike length of treated plants

Table II summarizes typical results obtained in the evaluation of compounds of the invention. A dash indicates that no determination of value was made.

TABLE III

Gametocidal Activity

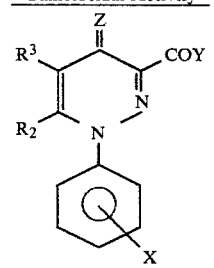

| Ex. No. | % Sterility (at lbs/A) | | | | | | | |
|---|---|---|---|---|---|---|---|---|
| | 8 | 4 | 2 | 1 | ½ | ¼ | ⅛ | 1/16 |
| 1 | — | 100 | 94 | 72 | 46+ 74 | 7+ 83 | — | — |
| 1A | — | 100 | 100 | 100 | 100 | 81 | — | — |
| 2 | 16 | 9 | 10 | 14 | 10 | — | — | — |
| 2A | 0 | 14 | 2 | 13 | 6 | — | — | — |
| 3 | — | 100 | 100 | 100 | 99 | — | — | — |
| 3A | 100 | 100 | 100 | 100 | 100 | 97+ 82 | — | — |
| 4 | — | 100 | 100 | 100 | 100 | — | — | — |
| 4A | 100 | 100 | 100 | 100 | 100+ 86 | 98+ 73 | — | — |
| 5 | — | 100 | 97 | 100 | 96 | — | — | — |
| 5A | 100 | 100 | 100 | 100 | 97+ | 99+ | — | — |

TABLE III-continued
Gametocidal Activity
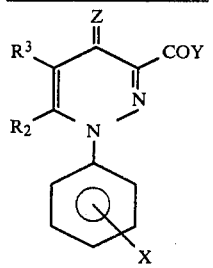
| Ex. No. | % Sterility (at lbs/A) | | | | | | | |
|---|---|---|---|---|---|---|---|---|
| | 8 | 4 | 2 | 1 | ½ | ¼ | ⅛ | 1/16 |
| 6 | 9 | 18 | — | — | 90 | 80 | — | — |
| 6a | 9 | 16 | 8 | 16 | 8 | — | — | — |
| 7 | 73 | 41 | — | — | — | — | — | — |
| 7A | 100 | 98+ 100 | 92+ 100 | 38 | 12 | — | | |
| 8 | 33 | 15 | — | — | — | — | — | — |
| 8A | 0 | 5 | 4 | 4 | 9 | — | — | — |
| 9 | 100 | 94 | — | — | — | — | — | — |
| 9A | 100 | 100+ 100 | 99+ 98 | 83+ 100 | 43+ 100 | — | — | — |
| 10 | 100 | — | — | — | — | — | — | |
| 10A | 100 | 100 | 100 | 100 | 95 | 66+ | — | — |
| 11 | 100 | — | — | — | — | — | — | |
| 11A | 100 | 98 | 92 | 16 | — | — | — | — |
| 12 | 100 | 100 | 96 | — | — | — | — | — |
| 12A | 100 | 100 | 100+ 45 | 100+ 34 | 100+ 90 | 100+ 72 | — | — |
| 13 | 86 | — | — | — | — | — | — | — |
| 13A | 100 | 100 | 74 | 64+ 73 | 94 | — | — | — |
| 14 | 75 | — | — | — | — | — | — | — |
| 14A | 100 | 100 | 100 | 100 | 97+ 90 | 40+ 97 | — | — |
| 15 | — | 6 | 2 | 10 | 7 | — | — | — |
| 15A | 9 | 3 | — | 8 | 7 | — | — | — |
| 16 | — | — | — | — | — | — | — | — |
| 16A | 100 | 100 | 100 | 100+ 65 | 84+ 73 | 15 | — | — |
| 17 | — | — | — | 82 | 48 | 32 | 35 | — |
| 17A | — | — | — | — | — | — | — | — |
| 18 | — | — | — | — | — | — | — | |
| 18A | — | — | — | 100 | 88 | 18 | 0 | — |
| 19A | — | 100 | 100 | 92 | 55 | — | — | — |
| 20 | — | — | — | — | 100 | 100 | 90 | 90 |
| 21 | — | — | — | — | 100 | 100 | 98 | 97 |
| 22 | — | — | — | — | 100 | 100 | 100 | 94 |
| 23 | — | — | 100+++ | 100+++ | 91+++ | 63+++ | — | — |
| 24 | 100 | — | 96 | — | 56 | — | 16 | — |
| 25 | NOT ACTIVE AT OR BELOW 8 lbs./Acre | | | | | | | |
| 26 | — | 4 | 3 | — | 0 | | | — |
| 27 | NOT ACTIVE AT OR BELOW 4 lbs./Acre | | | | | | | |
| 28 | — | — | — | 19 | 8 | 7 | 5 | 5 |
| 29 | — | — | — | 100 | 100 | 100 | 89 | 72 |
| 30 | — | — | — | 49 | 7 | 0 | 0 | — |
| 31 | ++ | — | ++ | — | 100 | — | 96 | — |
| 32 | — | — | — | 31 | 12 | 2 | 0 | — |
| 33 | 100++++ | — | 71++++ | — | — | — | — | — |
| 34 | NOT ACTIVE AT OR BELOW 4 lbs./Acre | | | | | | | |
| 35 | — | — | — | 79 | 85 | 19 | 0 | 2 |
| 36 | — | — | — | — | 7 | 6 | 8 | 4 |
| 37 | — | — | — | 96 | 93 | 76 | 42 | 2 |
| 38 | — | — | — | 92 | 83 | 82 | 61 | 70 |
| 39 | — | — | — | 63 | 9 | 1 | 0 | — |
| 40 | — | — | — | 83 | 34 | 0 | 4 | — |
| 41 | 94 | — | 70 | — | 37 | — | 10 | — |
| 42 | 100 | — | 99 | — | 67 | — | 9 | — |
| 43 | — | — | — | 100 | 100 | 100 | 98 | — |
| 44 | 100 | — | 100 | — | 100 | — | 99 | — |
| 45 | 49 | — | 21 | — | 5 | — | 7 | — |
| 46 | 100+++ | — | — | — | — | — | — | — |
| 47 | — | 16 | 0 | 0 | 0 | 0 | — | — |
| 48 | NOT ACTIVE AT OR BELOW 8 lbs./Acre | | | | | | | |
| 49 | — | — | — | 100 | 100 | 100 | 98 | — |

TABLE III-continued

Gametocidal Activity

| Ex. No. | % Sterility (at lbs/A) | | | | | | | |
|---|---|---|---|---|---|---|---|---|
| | 8 | 4 | 2 | 1 | ½ | ¼ | ⅛ | 1/16 |
| 50 | 100 | — | 100 | 100 | 100 | 98 | 95 | — |
| 51 | 100 | — | 100 | 88 | 37 | 2 | 0 | — |
| 52 | NOT ACTIVE AT OR BELOW 8 lbs./Acre | | | | | | | |
| 53 | 100 | — | 60 | — | 0 | 0 | — | — |

+multiple results that multiple separate tests were carried out
++spike emergence inhibited at 2 and 8 lb/A
+++soil drench test not foliar spray
++++HCl salt tested It is to be understood that changes and variations can be made without departing from the spirit and scope of the invention as defined by the appended claims.

I claim:

1. A method of inducing male sterility in a cereal grain or forage plant which comprises treating the plant prior to meiosis with an amount effective to produce male sterility in the plant of a compound of the formula

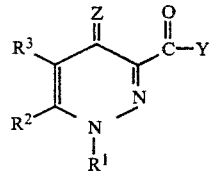

wherein
$R^1$ is an unsubstituted phenyl group or a phenyl group substituted with up to three substituents selected from the group consisting of halogen atoms, ($C_1$–$C_4$) alkyl, ($C_1$–$C_4$) alkoxy, ($C_1$–$C_4$) alkylthio, ($C_1$–$C_4$) alkylsulfinyl, ($C_1$–$C_4$) alkylsulfonyl or trifluoromethyl,
$R^2$ is a ($C_1$–$C_4$) alkyl group, or phenyl,
$R^3$ is a hydrogen atom, a ($C_1$–$C_4$) alkyl group, or a halogen atom, a benzyl group or a phenethyl group,
Z is oxygen or sulfur, and
Y is the group $Z'R^4$ or $NR^5R^6$
wherein $Z'$ is oxygen or sulfur,
$R^4$ is hydrogen, ($C_1$–$C_4$) alkyl, ($C_1$–$C_4$) alkoxyalkyl, cyclohexylmethyl, bromopropyl, phenyl or benzyl,
$R^5$ and $R^6$ are independently selected from the group consisting of hydrogen or ($C_1$–$C_4$) alkyl or ($C_1$–$C_4$) alkyl substituted with carboxyl or ($C_1$–$C_4$) alkoxycarbonyl, or when
$R^5$ is hydrogen, $R^6$ is hydroxyl, or an agronomically acceptable salt, ($C_1$–$C_{12}$) alkyl ester or mono or di($C_1$–$C_4$) alkyl amide thereof.

2. The method of claim 1 wherein $$\overset{O}{\underset{}{\overset{\|}{C}}}-Y$$

is a carboxyl group and Z is oxygen or an agronomically-acceptable salt or ($C_1$–$C_{12}$) alkyl ester thereof.

3. The method of claim 2 wherein $R^1$ is an unsubstituted phenyl group or a phenyl group substituted with one or two halogen atoms, a methyl group, a methoxy group, a methylthio or a trifluoromethyl group.

4. The method of claim 3 wherein $R^3$ is a hydrogen atom.

5. The method of claim 4 wherein $R^2$ is a methyl group.

6. The method of claim 5 wherein $R^1$ is a halophenyl group.

7. The method of claim 6 wherein $R^1$ is a 4-halophenyl group.

8. The method of claim 6 wherein $R^1$ is a 3-halophenyl group.

9. The method of claim 5 wherein $R^1$ is a trifluoromethyl phenyl group.

10. The method of claim 3 wherein $R^2$ is a methyl group and $R^3$ is a halogen atom.

11. The method of claim 10 wherein $R^1$ is a halophenyl group and $R^4$ is a bromine atom.

12. The method of claim 2 wherein the plant is wheat.
13. The method of claim 2 wherein the plant is barley.
14. The method of claim 2 wherein the plant is corn.
15. The method of claim 2 wherein the plant is rye.
16. The method of claim 2 wherein the plant is oat.
17. The method of claim 2 wherein the plant is rice.
18. The method of claim 2 wherein the plant is triticale.
19. The method of claim 2 wherein the plant is a forage crop.
20. The method of producing hybrid cereal grain seed which comprises treating a female parent of the cereal grain prior to meiosis with a compound of the formula

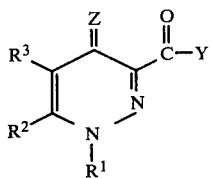

wherein $R^1$ is an unsubstituted phenyl group or a phenyl group substituted with up to three substituents selected from the group consisting of halogen atoms, $(C_1-C_4)$ alkyl, $(C_1-C_4)$ alkoxy, $(C_1-C_4)$ alkylthio, $(C_1-C_4)$ alkylsulfinyl, $(C_1-C_4)$ alkylsulfonyl or trifluoromethyl, $R^2$ is a $(C_1-C_4)$ alkyl group, or phenyl, $R^3$ is a hydrogen atom, a $(C_1-C_4)$ alkyl group, or a halogen atom, a benzyl group or a phenethyl group, Z is oxygen or sulfur, and Y is the group $Z'R^4$ or $NR^5R^6$ wherein $Z'$ is oxygen or sulfur, $R^4$ is hydrogen, $(C_1-C_4)$ alkyl, $(C_1-C_4)$ alkoxyalkyl, cyclohexyl, cyclohexylmethyl, bromopropyl, phenyl, or benzyl, $R^5$ and $R^6$ are independently selected from the group consisting of hydrogen or $(C_1-C_4)$ alkyl or $(C_1-C_4)$ alkyl substituted with carboxyl or $(C_1-C_4)$ alkoxycarbonyl, or when $R^5$ is hydrogen, $R^6$ is hydroxyl, or an agronomically acceptable salt, $(C_1-C_{12})$ alkyl ester or mono or di$(C_1-C_4)$ alkyl amide thereof.

21. The method of claim 20 wherein the amount sufficient to produce male sterility in the female parent is about 1/32 to about 20 pounds per acre.

22. The method of claim 21 wherein

is a carboxy group or an agronomically-acceptable salt or $(C_1-C_{12})$ alkyl ester thereof, $R^1$ is an unsubstituted phenyl group or a phenyl group substituted with one or two halogen atoms, a methyl group, a methoxy group, a methylthio group, or a trifluoromethyl group, $R^2$ is a methyl group, and $R^3$ is a hydrogen atom or a halogen atom.

23. The method of claim 21 wherein the cereal grain is selected from wheat, barley, rice, corn, oat, rye or triticale.

* * * * *

UNITED STATES PATENT AND TRADEMARK OFFICE
CERTIFICATE OF CORRECTION

PATENT NO. : 4,345,934
DATED : August 24, 1982
INVENTOR(S) : Ted. T. Fujimoto

It is certified that error appears in the above—identified patent and that said Letters Patent is hereby corrected as shown below:

Claim 11, line 2, "$R^4$" should be -- $R^3$ --.

Signed and Sealed this

Twenty-third Day of November 1982

[SEAL]

Attest:

GERALD J. MOSSINGHOFF

Attesting Officer — Commissioner of Patents and Trademarks